United States Patent
MacPherson, III et al.

(10) Patent No.: US 7,703,344 B2
(45) Date of Patent: Apr. 27, 2010

(54) COUPLER FOR ATTACHMENT OF SAMPLING TUBES TO DUCT DETECTOR

(75) Inventors: William A. MacPherson, III, Wasco, IL (US); James M. Murphy, St. Charles, IL (US)

(73) Assignee: Honeywell International Inc., Morristown, NJ (US)

( * ) Notice: Subject to any disclaimer, the term of this patent is extended or adjusted under 35 U.S.C. 154(b) by 258 days.

(21) Appl. No.: 11/496,365

(22) Filed: Jul. 31, 2006

(65) Prior Publication Data

US 2008/0022753 A1      Jan. 31, 2008

(51) Int. Cl.
 *G01N 1/10* (2006.01)
(52) U.S. Cl. ............ 73/864.73; 73/863; 73/863.81
(58) Field of Classification Search .......... 73/31.01
 See application file for complete search history.

(56) References Cited

U.S. PATENT DOCUMENTS

| | | | | |
|---|---|---|---|---|
| 2,464,546 | A | * | 3/1949 | Albright ............... 374/15 |
| 4,541,657 | A | * | 9/1985 | Smyth ............... 285/305 |
| 4,634,197 | A | * | 1/1987 | Horlacher, Jr. ........... 439/192 |
| 4,907,829 | A | | 3/1990 | Spangenberg |
| D327,228 | S | | 6/1992 | Fenne |
| 5,844,148 | A | * | 12/1998 | Klein et al. ............ 73/863.82 |
| 6,124,795 | A | | 9/2000 | Bernau et al. |
| 6,741,181 | B2 | | 5/2004 | Skaggs |
| 7,204,522 | B2 | | 9/2004 | Hall |
| 2004/0189003 | A1 | | 9/2004 | Hall et al. |

FOREIGN PATENT DOCUMENTS

GB      2 347 541 A      9/2000

OTHER PUBLICATIONS

International Search Report and Written Opinion of The International Searching Authority, mailed Apr. 4, 2008 corresponding to International application No. PCT/US2007/074315.
Air Products and Controls Inc., Installation and Maintenance Instructions for SL-2000 Series Duct Smoke Detectors, published at least prior to filing date of this application.
Air Products and Controls Inc., Product Overview and Specifications for SL-2000 Series Duct Smoke Detectors, published at least prior to filing date of this application.
Telaire, Superduct Smoke Detectors Product Description and Diagram, published at least prior to filing date of this application.
Edwards Systems Technology, Intelligent Duct Smoke Detector Product Description and Specifications, published at least prior to filing date of this application.

* cited by examiner

*Primary Examiner*—Hezron Williams
*Assistant Examiner*—Mark Shabman
(74) *Attorney, Agent, or Firm*—Husch Blackwell Sanders Welsh & Katz

(57) ABSTRACT

A duct detector includes sampling tubes which slidably engage the detector with a fixed orientation to facilitate fluid flow. The tubes have a connector portion and a conduit portion. The connector portion and the conduit portion engage one another with a predetermined orientation.

21 Claims, 21 Drawing Sheets

US 7,703,344 B2

COUPLER FOR ATTACHMENT OF SAMPLING TUBES TO DUCT DETECTOR

FIELD

The invention pertains to duct-type detectors. More particularly, the invention pertains to such detectors with sample tubes that can be readily installed with an appropriate orientation without tools.

BACKGROUND

It's been recognized that duct mountable ambient condition detectors can be useful in ambient condition monitoring systems, such as fire detection systems. Such detectors, which might respond to airborne smoke or gases, can be coupled to ducts which might be part of an HVAC which extends through a building or region being monitored. Such detectors are disclosed for example in Berneau et al., U.S. Pat. No. 6,124,795 entitled Detector Interconnect System which issued Sep. 26, 2000, and which is assigned to the assignee hereof, as well as Fenne Design Pat. DES. 327,228 which issued Jun. 23, 1992, and is also assigned to the assignee hereof. The '795 and '228 patents are incorporated herein by reference.

Known duct detectors require one or more tubular conduits to redirect air from inside the associated duct, part of a building ventilation system, to the detector. The conduits or sampling tubes are formed with openings aligned along their length. The openings allow air to flow down the tube to the detector and return again to the system.

To ensure proper operation of the detector the openings must be aligned with the oncoming flow inside the system. The conduit must therefore be coupled to the detector housing or enclosure in a way that provides correct alignment and is secure to prevent disengagement or movement after installation.

Known configurations used to couple the conduits to detector housings or enclosures tend to be cumbersome and time consuming to install. Fasteners are often used to retain the sampling tubes. These usually require the use of hand tools and can be difficult to work with in the small dark spaces the detectors are frequently installed. Often the detector cover must be removed to install the tubes and gain access to the fasteners, adding to the time and effort required for installation. Should the sampling tubes be installed in the wrong position the cover must again be removed to release the tube and reposition it correctly.

One known coupling device is a formed flange fitted around the outer diameter of the conduit and fixed in place by a weld or a fastener as illustrated in FIGS. 1A & 1B. Another is a rectangular tab formed into the end of the conduit that is guided through slots and aligned with notches in the detector housing as in FIG. 2.

Both of the configurations of FIGS. 1A, 1B and 2 have disadvantages. Specialized production equipment is required to attach a separate flange or punch and form a tab. The equipment can be costly to purchase, require frequent maintenance, and may have high operating cost. A formed tab protruding from the end of the tube may be sharp and could injure an operator producing the tubes or a technician handling them during installation. An improved coupler design which eliminates the need for fastening or welding and utilizes less costly production equipment would be desirable.

Many man-hours could be saved and installation costs reduced if the coupling of these tubes was simple, quick, and did not require the use of tools or removal of the detector cover. In addition, insertion from both sides would be desirable.

HVAC systems used to condition air-within a building and often contain cooling coils, and humidifiers which expose the detector and sampling tubes to moisture. Condensation on the any surface of the sampling tubes could collect inside the detector and cause the detector to malfunction. Current sampling tube designs do little to prevent condensation from entering the detector enclosure. It would be desirable to provide a coupler that would route small amounts of moisture away from the detector and prevent accumulation in the enclosure.

DETAILED DESCRIPTION

Figure 1A:
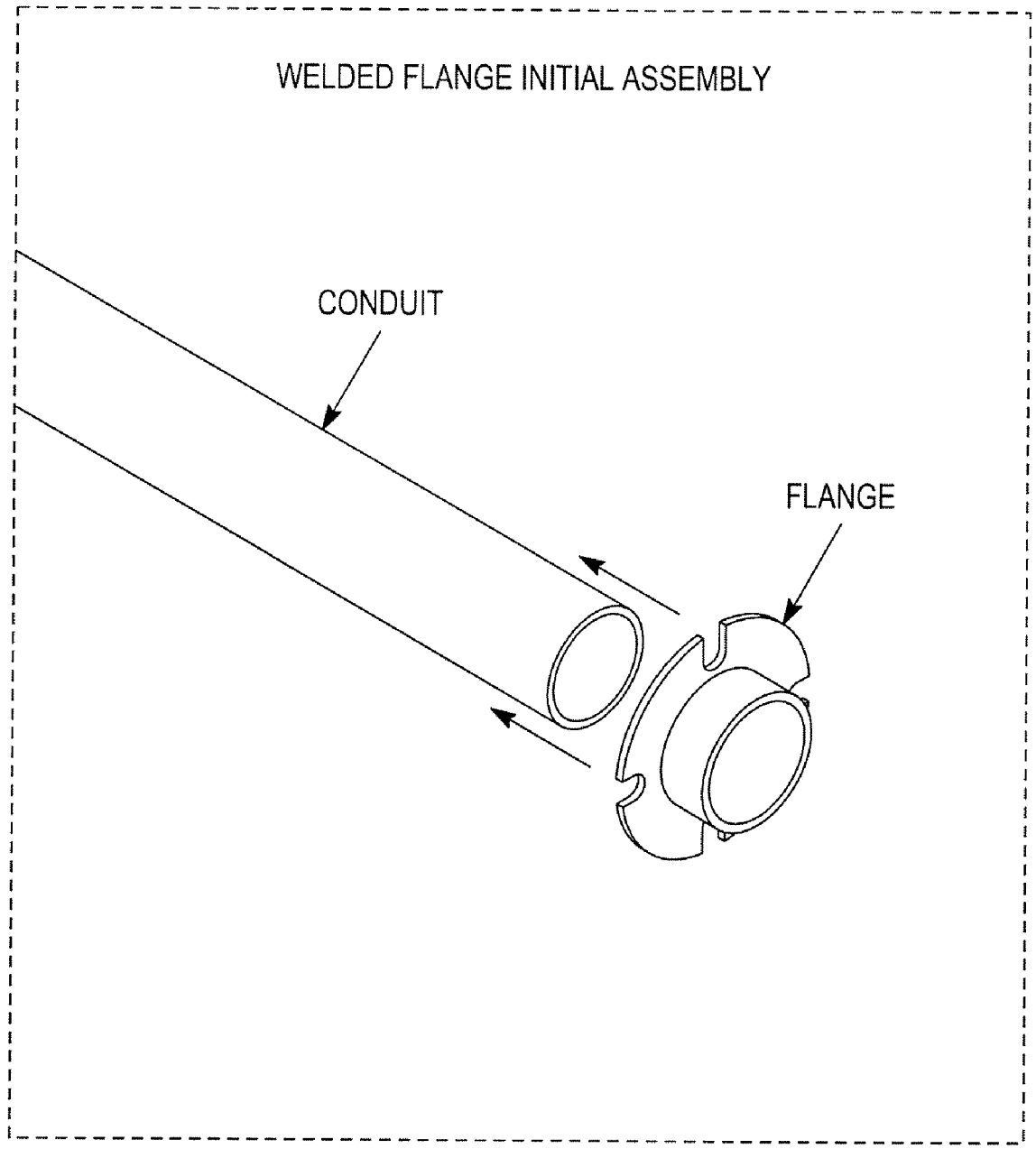
FIGS. 1A, 1B taken together illustrate one form of a prior art sampling tube.
Figure 1B:
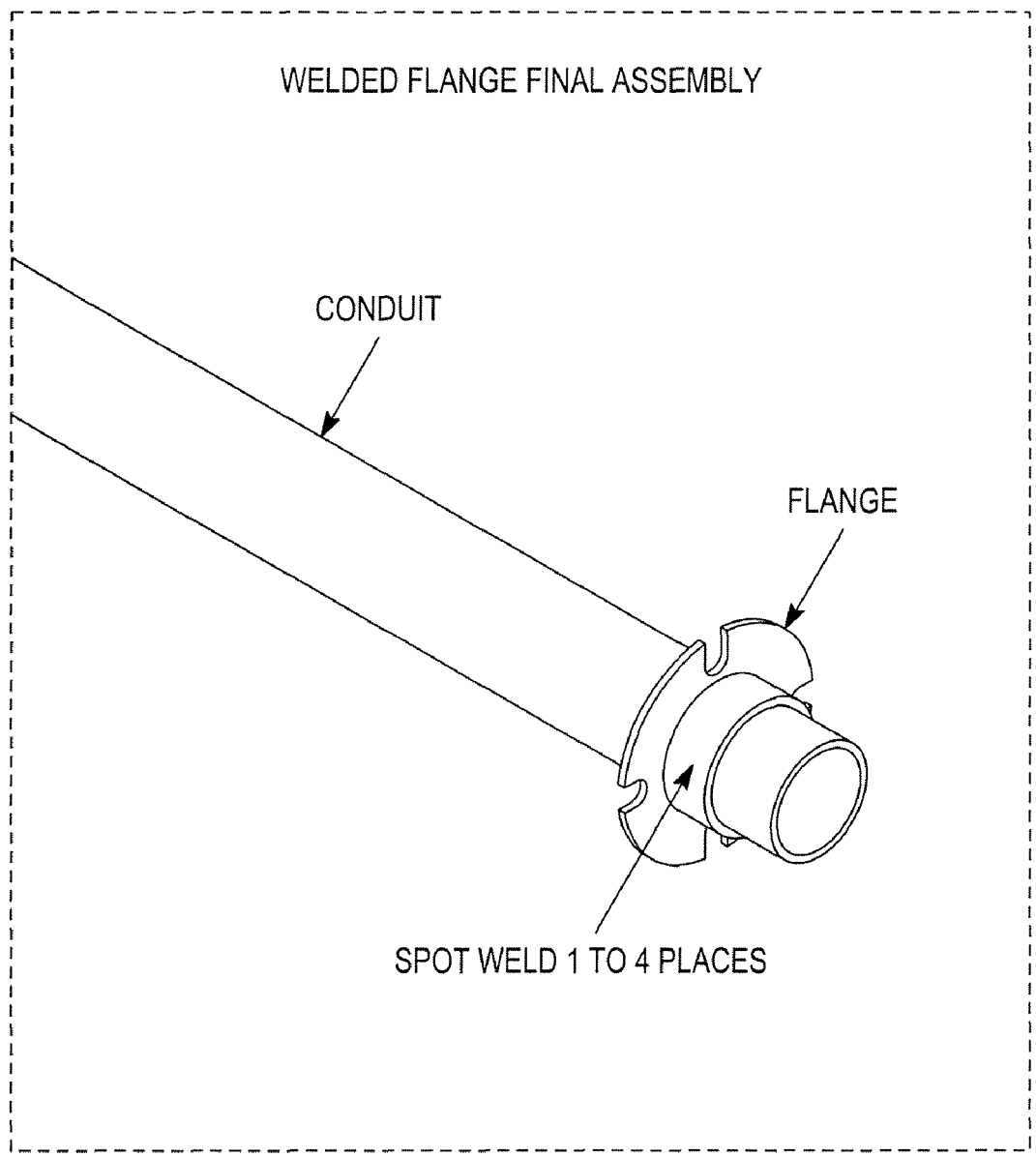
Figure 2:
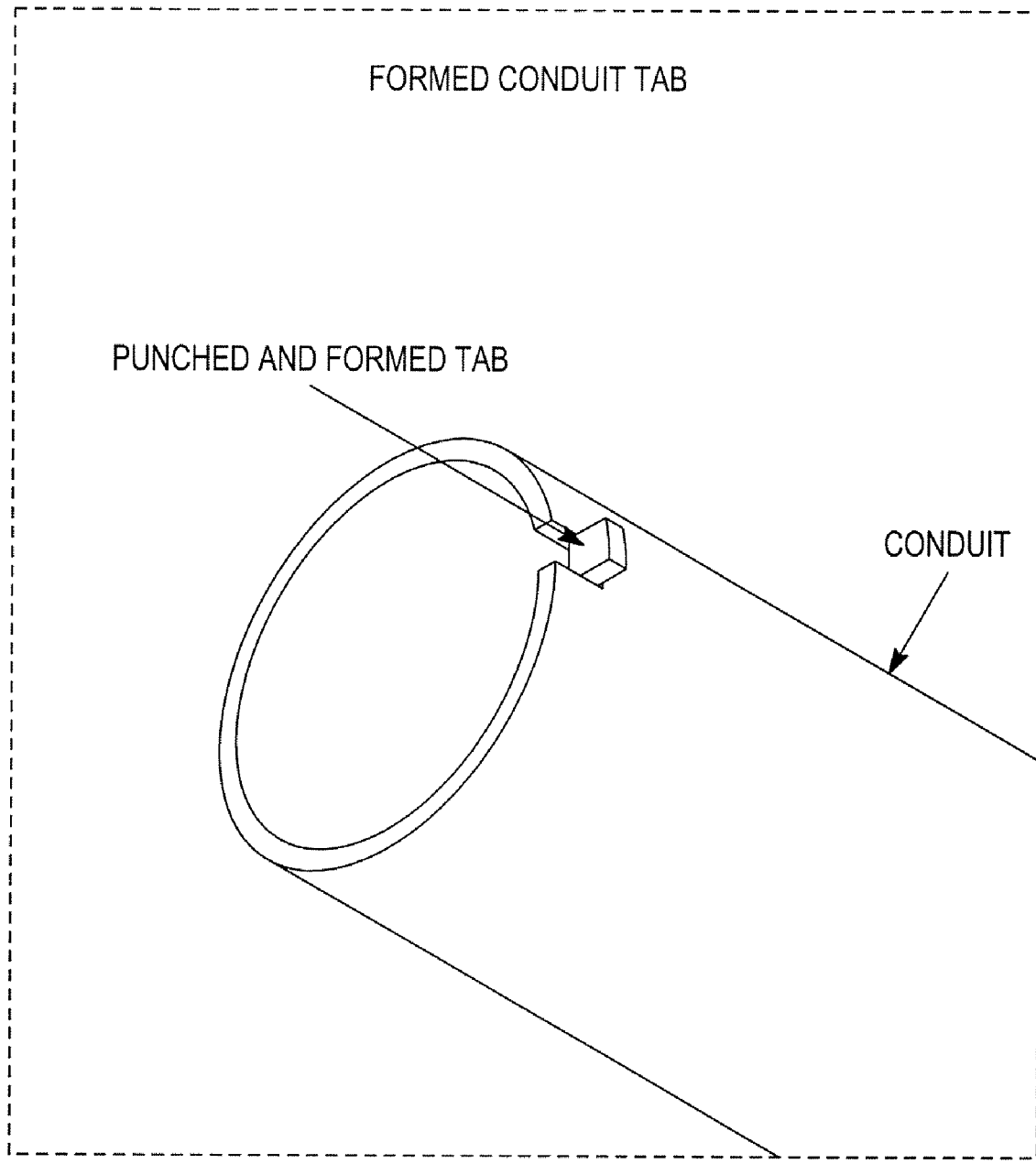
FIG. 2 illustrates another form of a prior art sampling tube.

While embodiments of this invention can take many different forms, specific embodiments thereof are shown in the drawings and will be described herein in detail with the understanding that the present disclosure is to be considered as an exemplification of the principles of the invention, as well as the best mode of practicing same, and is not intended to limit the invention to the specific embodiment illustrated.

Sampling tubes which embody the present invention can in one aspect provide a visual indication of proper alignment with the oncoming air flow, facilitate coupling and uncoupling to the detector enclosure in a less laborious and time consuming fashion than previous designs, and eliminate the need for fasteners or hand tools. Embodiments of the present coupler also provide protection against the ingress of water into the detector due to condensation on the surface of the tubes.

In another aspect of the invention, the present coupler can be injection molded of a durable thermoplastic. Such couplers could include integral, molded, features for permanent assembly to a tubular conduit, coupling to a detector enclosure, and alignment to the oncoming flow. Several embodiments of couplers that embody the present invention are described below.

One embodiment of a coupler contains an integral flexible member or cantilever snap that would mate with an opening in the conduit. The mating feature could be a hole, drilled or punched through the outer surface of the conduit.

Another embodiment of the coupler would include a threaded connection. The coupler could be produced with integral threads on either an internal or external surface. The conduit could contain a formed feature to engage the molded threads as the coupler is rotated onto the ends of the conduit similar to a threaded pipe fitting. The coupler could also be designed for a press fit to the conduit.

A preferred coupler embodiment would be one that easily assembles without tools. This could be accomplished by forming a detail in the conduit wall which fits into a mating opening in the coupler. The conduit could be formed prior to assembly of the coupler or after.

The coupler could be designed such that a portion of the inner diameter would interfere with the formed detail. The coupler could be assembled over the end of the tube by hand to the point where the mating features are in contact, placed into a fixture, and pressed into final position. The parts would snap together, permanently attaching one to the other.

The forming operation could, in another embodiment, be performed after the coupler has been assembled to the tube through an opening in the coupler or on the outside surface of the conduit. A secondary process could be used to create a deformation or a recess. Either could be formed without piercing the tube wall or punching a hole.

Once assembled the conduit and coupler form a sampling tube which is then coupled to the enclosure of the duct detector. The detector enclosure includes a housing and cover, which are sealed to prevent mixing of air from inside and outside the HVAC system. A smoke or gas sensor is carried in the housing. The detector housing includes integral ports designed to receive the sampling tubes from either side of the enclosure.

Installation from the back of the enclosure eliminates a need to remove the detector cover thereby simplifying the installation process and future replacement. These ports have an internal bore that closely fits the predetermined shape of the coupler. The predetermined shape provides alignment of the tube to the airflow when the detector is mounted on a duct with one of the available orientations. An indicator on the coupler is pointed into the airflow and verifies the alignment.

Each port contains one or more cantilevered latches to lock the coupler into place and prevent disengagement or inadvertent removal of the sampling tube. These latches are easily actuated by hand and allow easy removal of the tubes for cleaning or repositioning.

The coupler also prevents or minimizes an accumulation of moisture in the detector enclosure. This is accomplished by providing a small amount of clearance between the mating surfaces of the coupler and conduit. The clearance provides a path away from the housing for condensation that has collected on the tube and is forced in the direction of the detector due to airflow in the duct.

Figure 3:
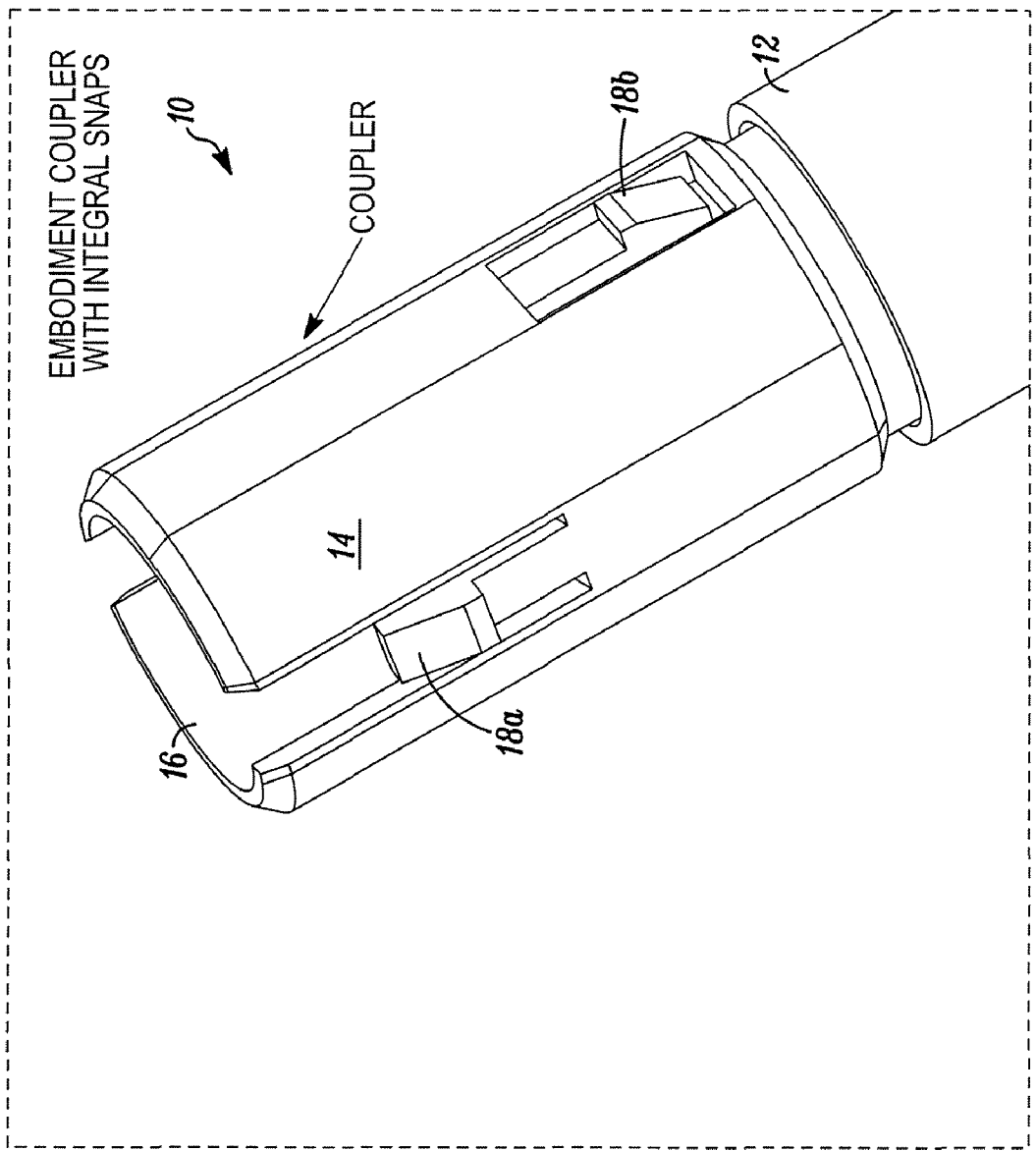
FIG. 3 illustrates a sampling tube in accordance with the present invention.

FIG. 3 illustrates a coupler 10 which can be connected to a hollow conduit 12, which could include openings for inflow or outflow of ambient atmosphere as would be understood by those of skill in the art. The coupler 10 has an elongated, hollow cylindrical body 14 with an internal flow path 16.

The housing 14 carries first and second integrally formed flexible attachment elements or cantilever snaps 18a, 18b. One of the snaps, such as 18b, could mate with an appropriately shaped opening in the conduit 12. The other snap, such as 18a, could mate with a housing or an enclosure for a respective duct-type detector. The mating feature in the conduit 12 with which the snap 18b engages could be a hole or other opening which has been drill punched, molded or otherwise formed in the conduit 12.

Figure 4A:
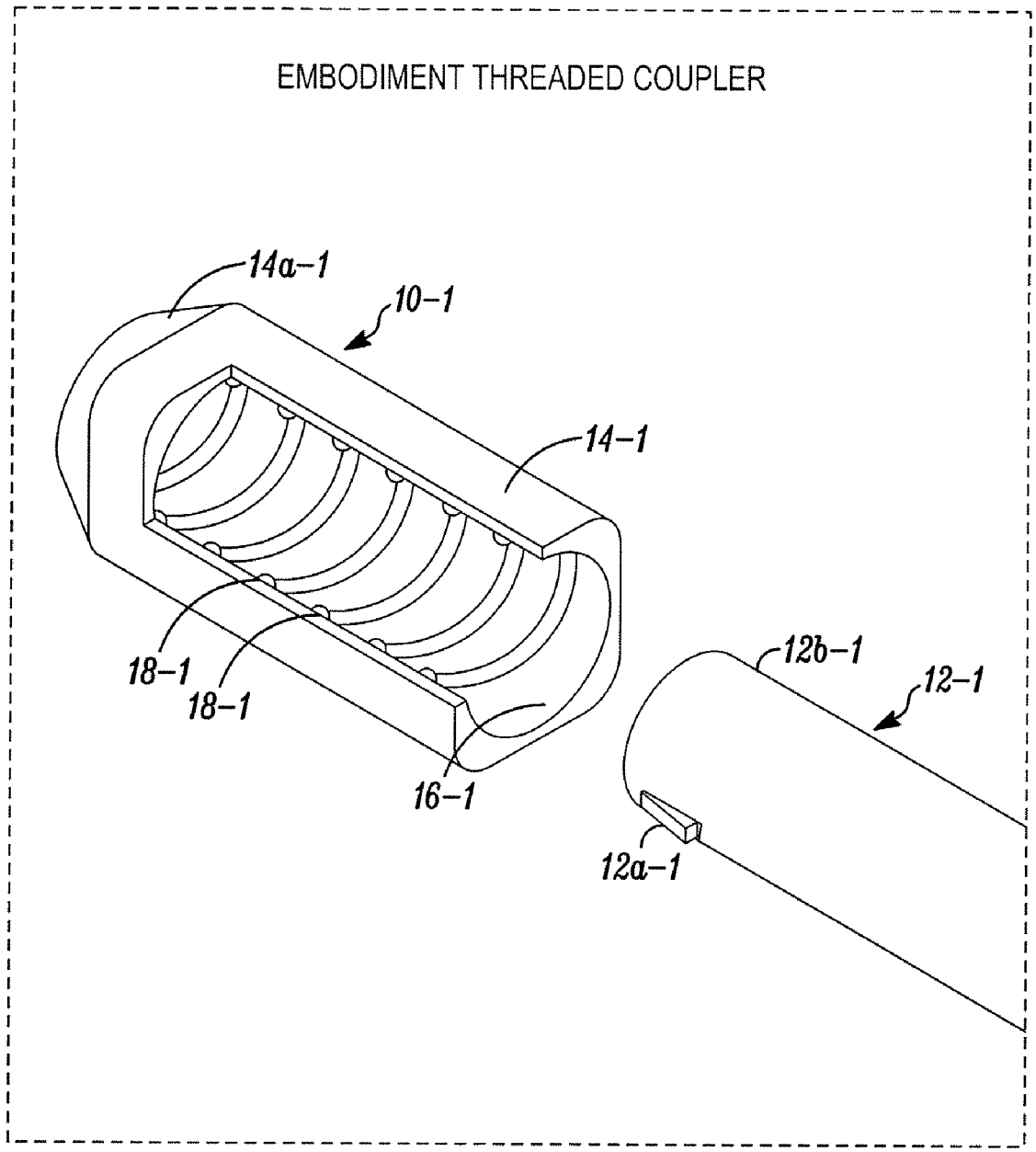
FIGS. 4A, 4B taken together illustrate another sampling tube in accordance with the invention.
Figure 4B:
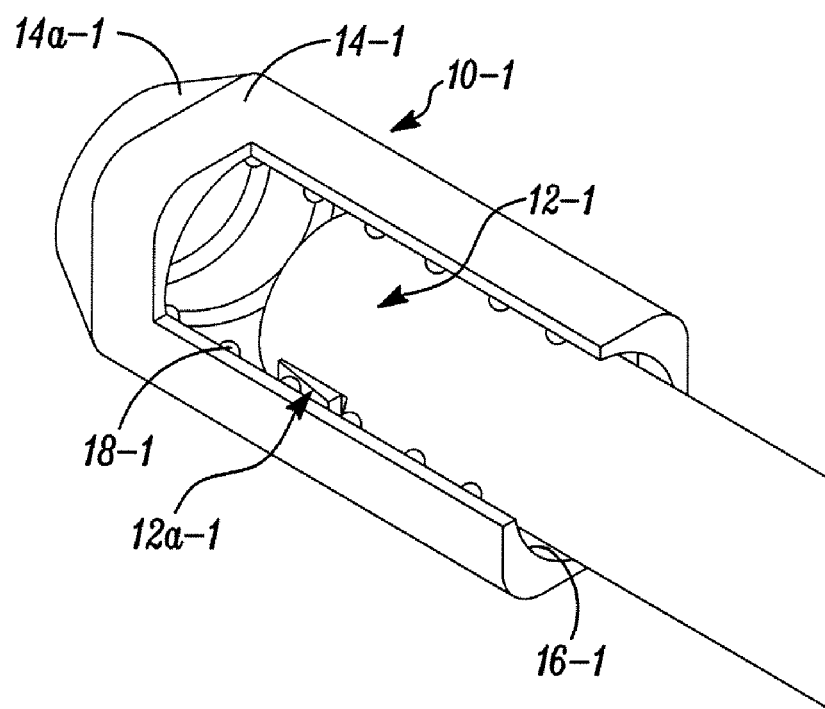

FIGS. 4A, 4B illustrate a threaded form of a coupler 10-1 which can rotatably engage a respective hollow conduit 12-1. As illustrated in FIGS. 4A, 4B a hollow body portion 14-1 of coupler 10-1 includes a set of internal integrally molded threads 18-1 which rotatably engage a feature 12a-1 formed on an end 12b-1 of the conduit 12-1.

The coupler 14-1 can be rotated onto the conduit 12-1, best seen in FIG. 4B, through the engagement of the threads 18-1 and the feature 12a-1. End 14a-1 can slideably engage and latch, using latches such as the latches 18a of FIG. 3, to a respective housing or enclosure of a duct detector.

Figure 5A:
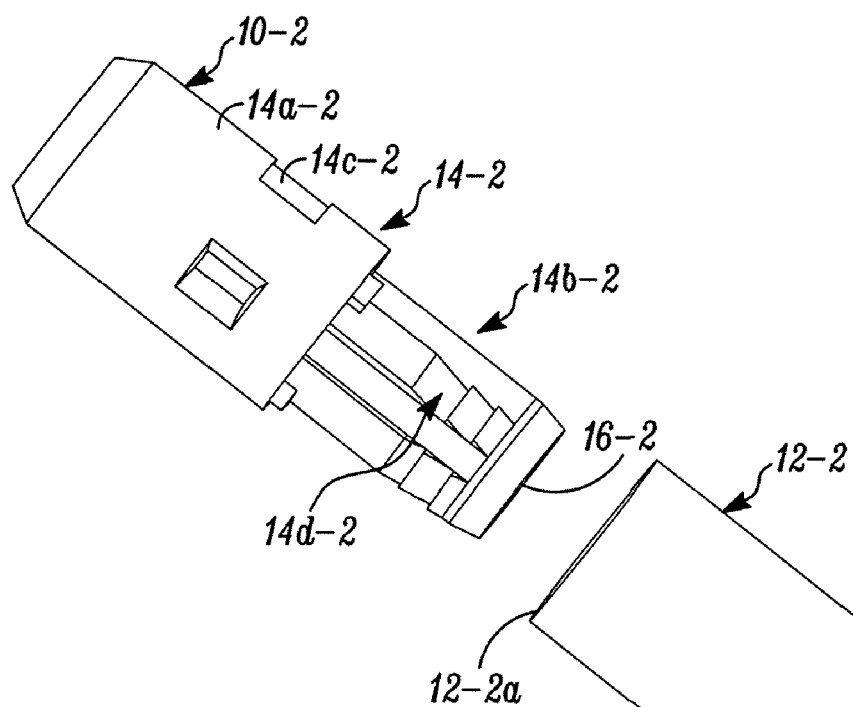
FIGS. 5A, 5B taken together illustrate yet another sampling tube in accordance with the invention.
Figure 5B:
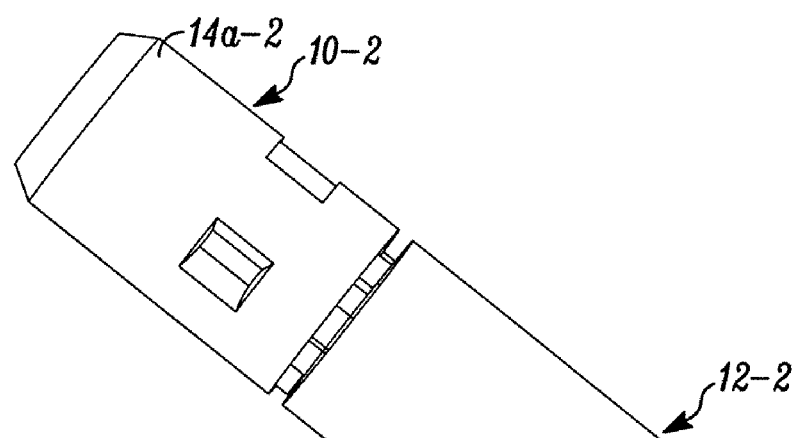

FIGS. 5A, 5B illustrate an embodiment of a coupler 10-2 which engages a respective conduit 12-2 with a press fit or interference fit. The coupler 10-2 is hollow with an internal channel 16-2.

The coupler 10-2 has a detector end 14a-2 which carries an engagement feature, or features 14c-2 which slideably engage with and lock to a respective detector housing or enclosure.

The coupler 10-2 has a displaced conduit related end 14b-2 which could be tapered and/or carry engagement features 14d-2 to slideably engage an internal channel 12-2a of the conduit 12-2. As illustrated in FIG. 5B, when the end 14b-2 is press fit into the channel 12-2a of the conduit 12-2 the housing or enclosure end 14a-2 continues to be exposed so as to be slideably engageable with the respective detector after the coupler 10-2 and the conduit 12-2 have been assembled together.

Figure 6A:
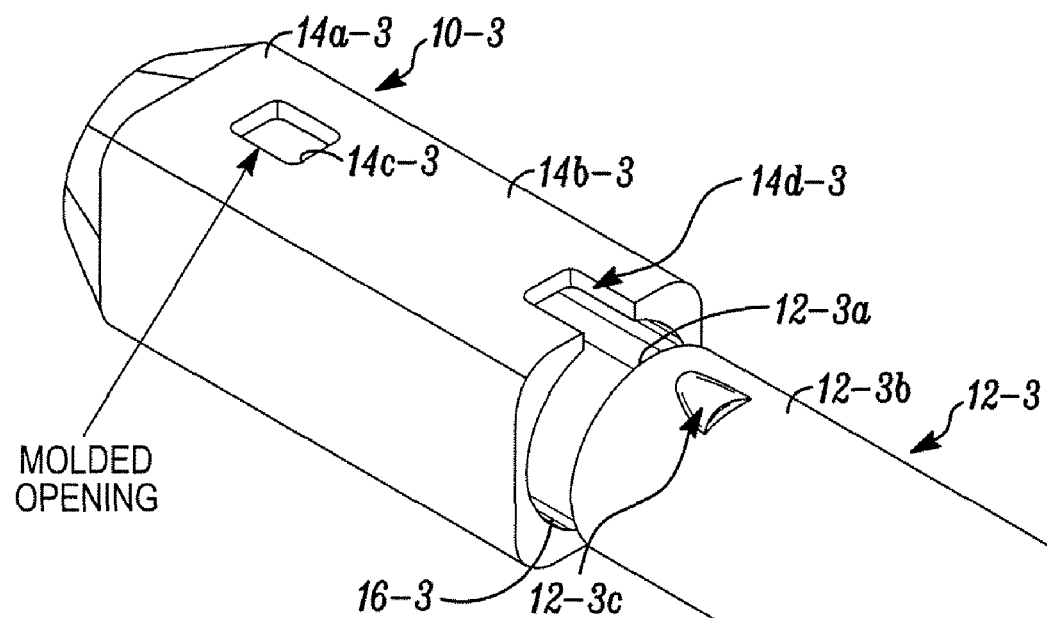
FIGS. 6A, 6B taken together illustrate yet another form of a sampling tube in accordance with the invention.
Figure 6B:
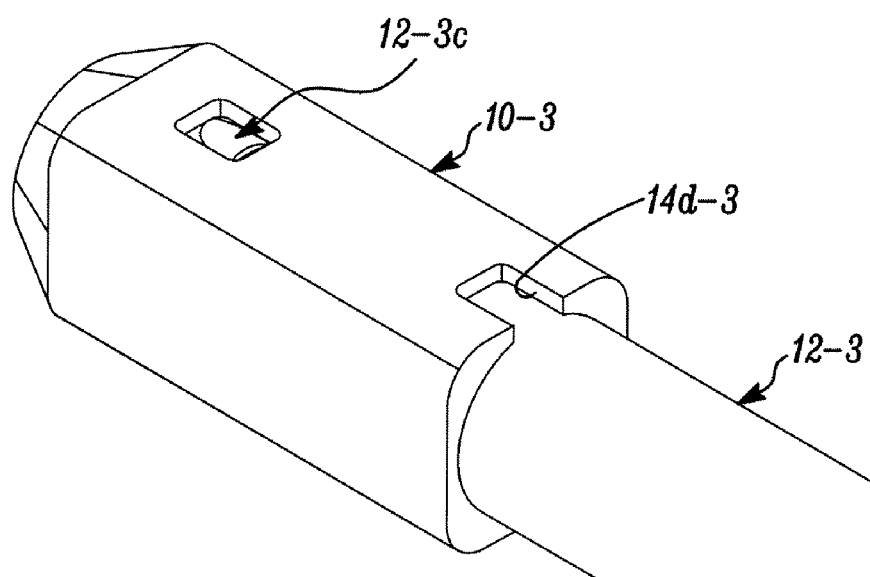

FIGS. 6A, 6B illustrate a preferred embodiment for aligning and locking a coupler 10-3 to a respective conduit 12-3.

The coupler 10-3 has first and second spaced apart ends 14a-3, 14b-3. As is the case with the couplers discussed previously, the coupler 10-3 is hollow with an internal flow channel 16-3. A locking feature, such as a molded opening 14c-3 is carried adjacent to end 14a-3. An alignment feature 14d-3 is formed in the end 14b-3 of coupler 10-3.

The conduit 12-3 carries an alignment and locking feature 12-3c. The coupler 10-3 is assembled to the conduit 12-3 by slideably engaging end 12-3b. The feature 12-3c is slid into engagement with the alignment feature 14b-3 either manually or with the use of a fixture as would be understood by those of skill in the art. A fixture could then be used to slide the body 14-3 of the coupler 10-3 onto the conduit 12-3 such that the feature 12-3c is slid through a channel 16-3 to the molded opening 14c-3 as a final position. The coupler 10-3 and the conduit 10-3 then snap together and are permanently attached to one another.

Those of skill will understand that the features 12-3c and 14c-3 could be formed in a variety of shapes and orientations without departing from the spirit and scope of the present invention. Additionally, instead of a protrusion, feature 12-3c could be formed as a depression and the opening or port 14c-3 could be formed as an internally extending mating intrusion. It will be understood that the end 14a-3 of the coupler 10-3 could also carry detector housing engagement features such as 14c-2 of FIG. 5A.

Figure 7A:
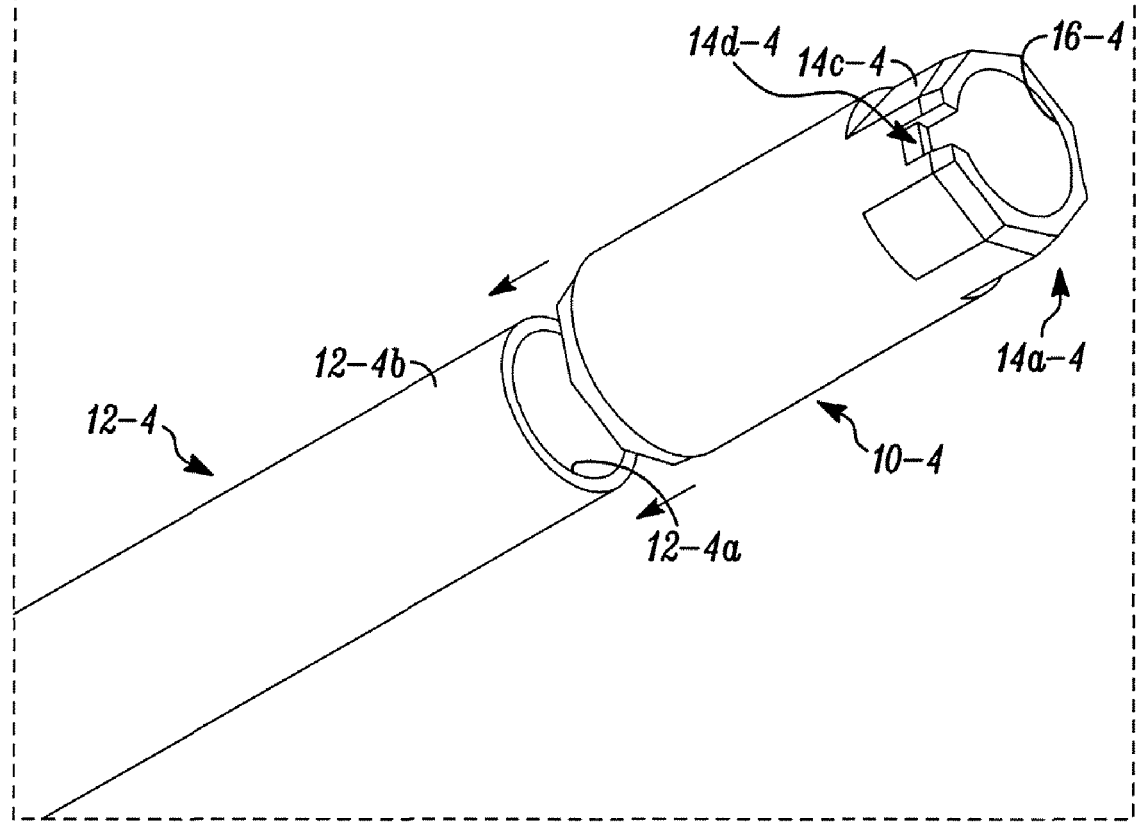
FIGS. 7A, 7B, 7C illustrate yet another form of a sampling tube in accordance with the invention.
Figure 7B:
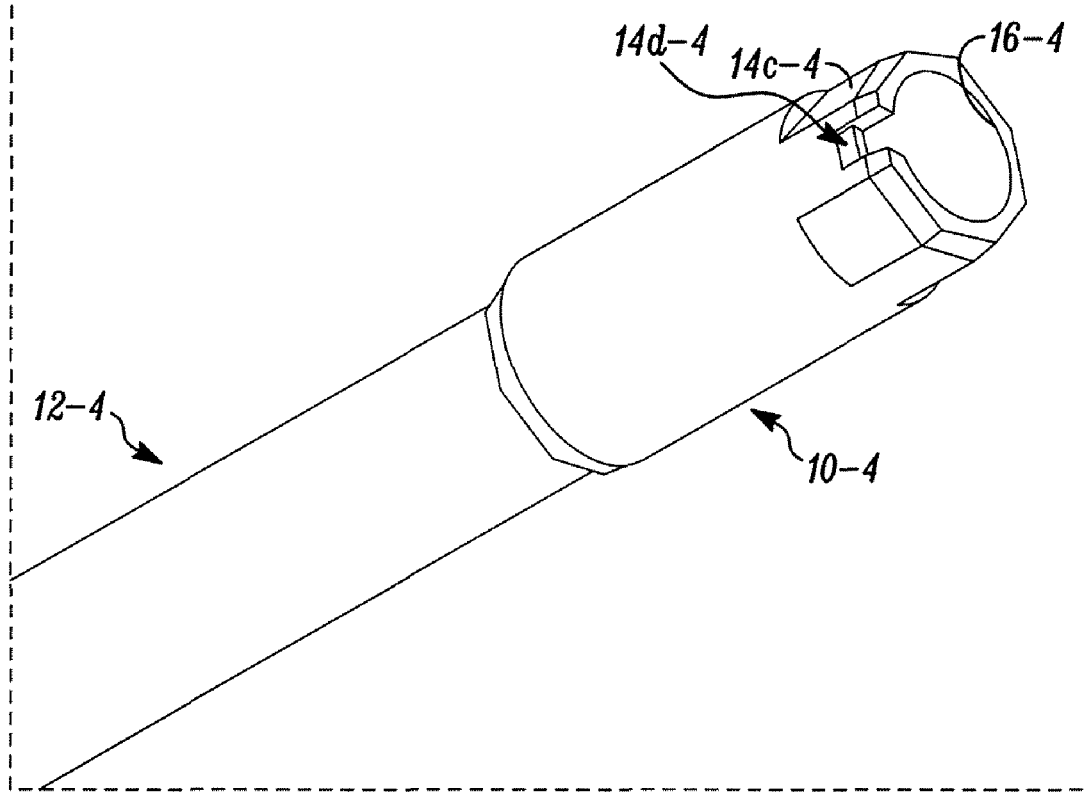
Figure 7C:
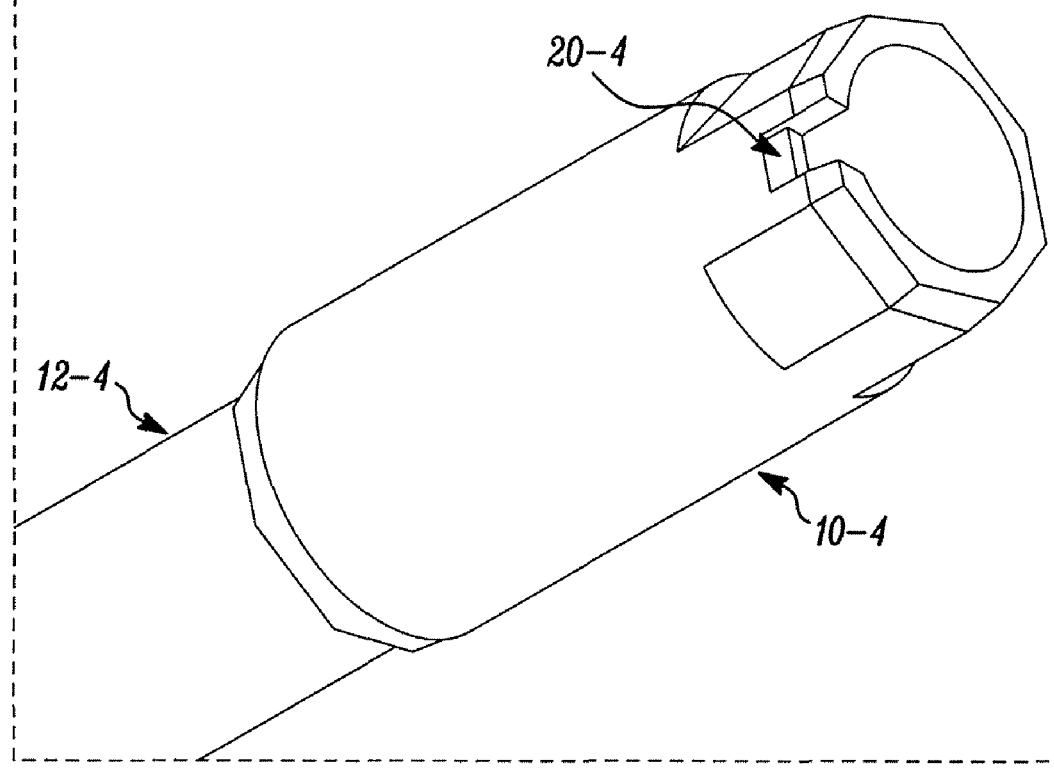

FIGS. 7A, 7B and 7C illustrate an alternate embodiment of a coupler 10-4 which is locked to a respective conduit 12-4 by a locking feature 20-4 formed in the end of the conduit 12-4. In the embodiment of FIGS. 7A-7C the coupler 10-4 is slideably received over the hollow conduit 12-4 on the end 14-4b.

In the embodiment of FIGS. 7A-7C the locking feature 20-4 is formed through an opening 14d-4 formed in an end 14a-4 of the coupler 10-4. It will be understood that the opening 14d-4 illustrated having a rectangular aspect in FIGS. 7A-7C could be formed with a variety of shapes and configurations without departing from the spirit and scope of the invention.

As illustrated in FIG. 7B, the end 12-4b of the conduit 12-4 is positioned adjacent to the opening 14d-4. Subsequently, a locking feature 20-4 is formed in the end 12-4b of the conduit 12-4. The locking feature 20-4 engages a surface of the opening 14d-4 locking the conduit to the coupler 10-4. The coupler 10-4, as illustrated in FIG. 7A-7C can carry detector housing engagement features 14c-4 at the detector engagement end 14a-4.

Figure 8A:
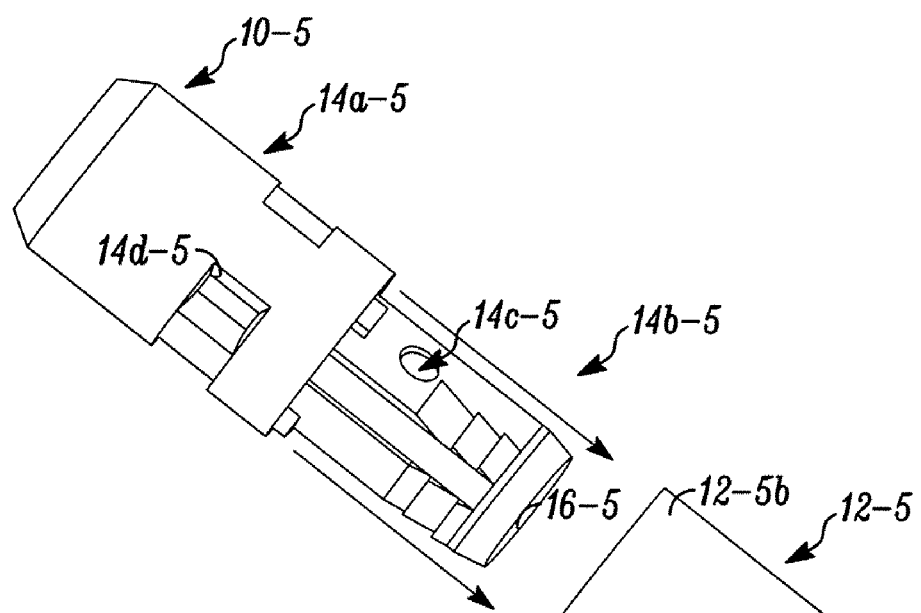
FIGS. 8A, 8B taken together illustrate yet another form of a sampling tube in accordance with the invention.
Figure 8B:
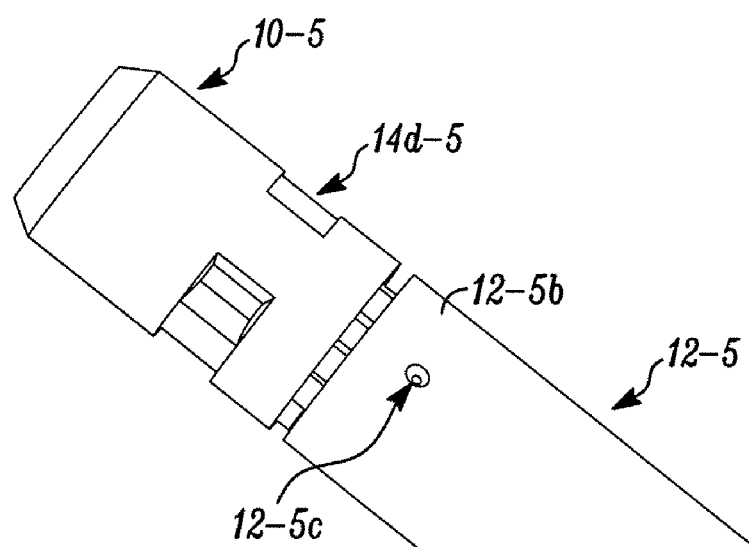

Alternate configurations come within the spirit and scope of the present invention. FIGS. 8A, 8B illustrate one such alternate.

With respect to FIGS. 8A, 8B a coupler 10-5 slideably engages a respective conduit 12-5. A conduit receiving end 14b-5 of the coupler 10-5 carries a molded or formed feature or depression 14c-5.

When the conduit 12-5 is appropriately positioned on the end 14b-5, as illustrated at FIG. 8B, a depression or formed feature 12-5c can be formed on the end 12-5b of the conduit 12-5 thereby locking the conduit to the coupler. The feature 12-5c engages the depression 14c-5 of the coupler. Prior to forming the feature 12-5c the radial location of the conduit 14-5 and the axially located openings thereon (to permit ingress and egress of the ambient atmosphere being sensed) is established relative to the detector housing locking features 14d-5 of the coupler 10-5.

Figure 9:
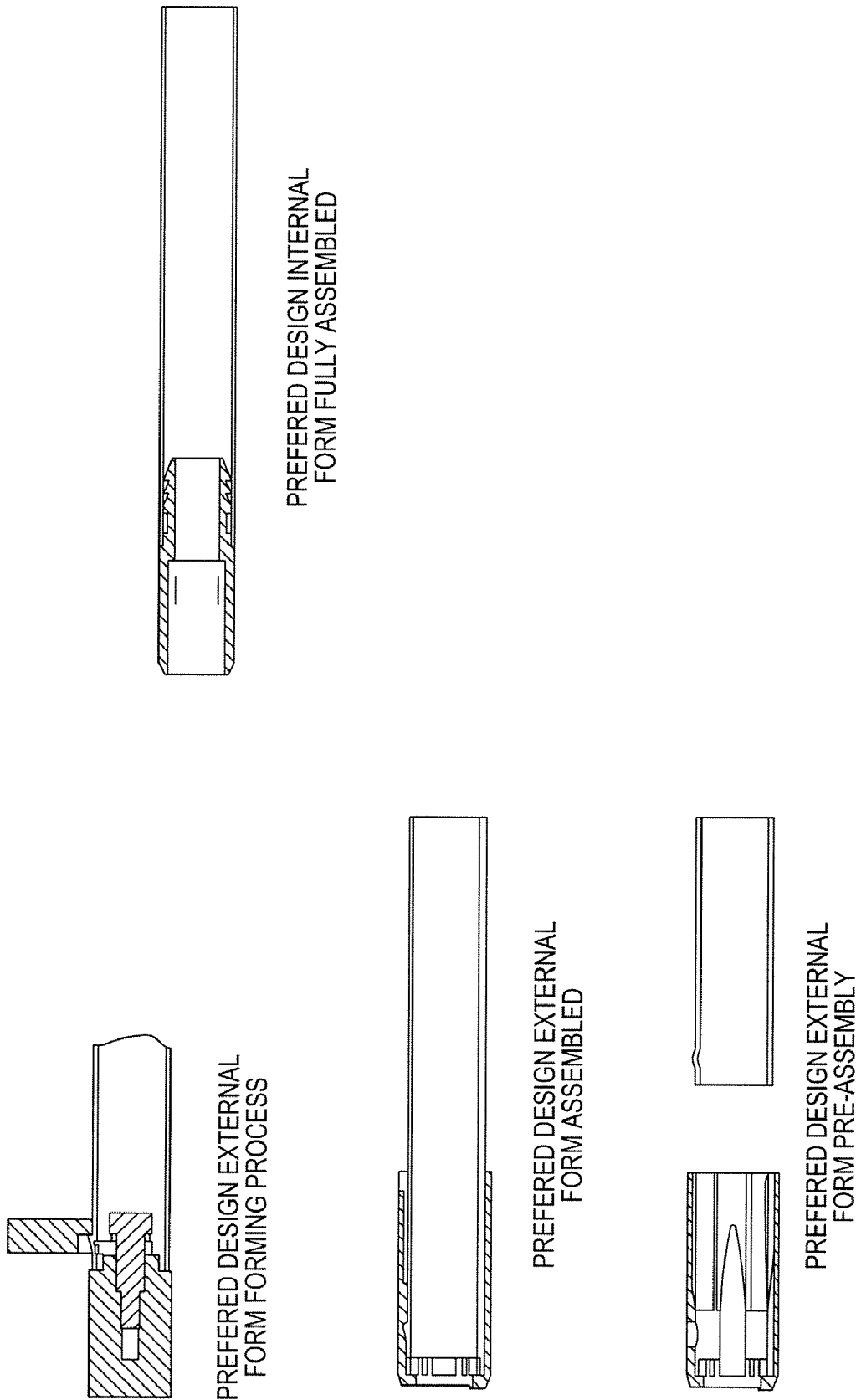
FIG. 9 illustrates various aspects of a process for attaching a conduit to a connector to form a sampling tube.

FIG. 9 illustrates cross-sectional views of the conduit, such as conduit 12-5, and coupler, such as the coupler 10-5, after the locking feature, such as the feature 12-5c of FIG. 8B, has been formed to lock the conduit to the respective coupler.

Figure 10A:
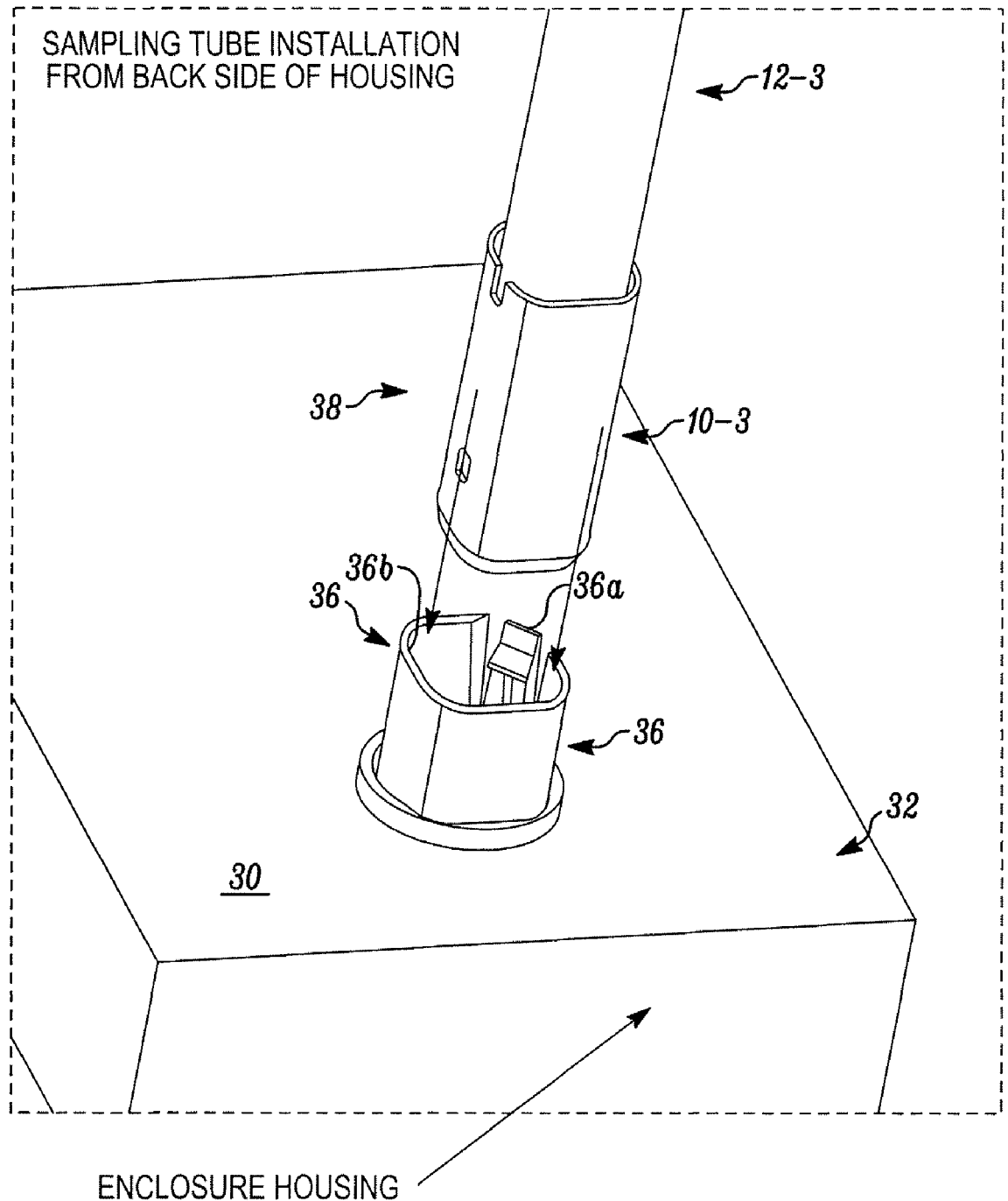
FIG. 10A illustrates attachment of the sampling tube from the back side of the enclosure.
Figure 10B:
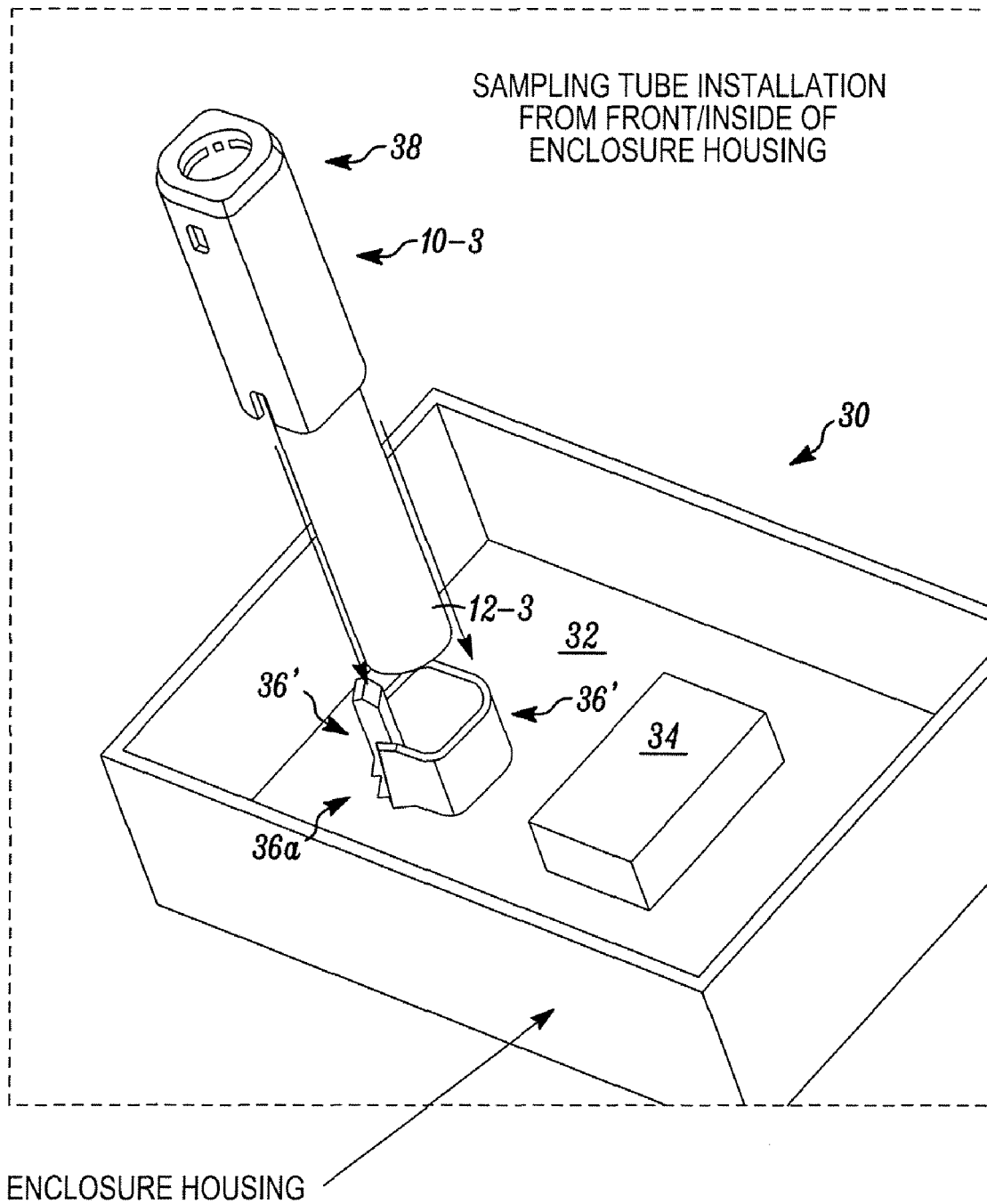
FIG. 10B illustrates attachment of the sampling tube from the front of the enclosure after removal of the cover.
Figure 10C:
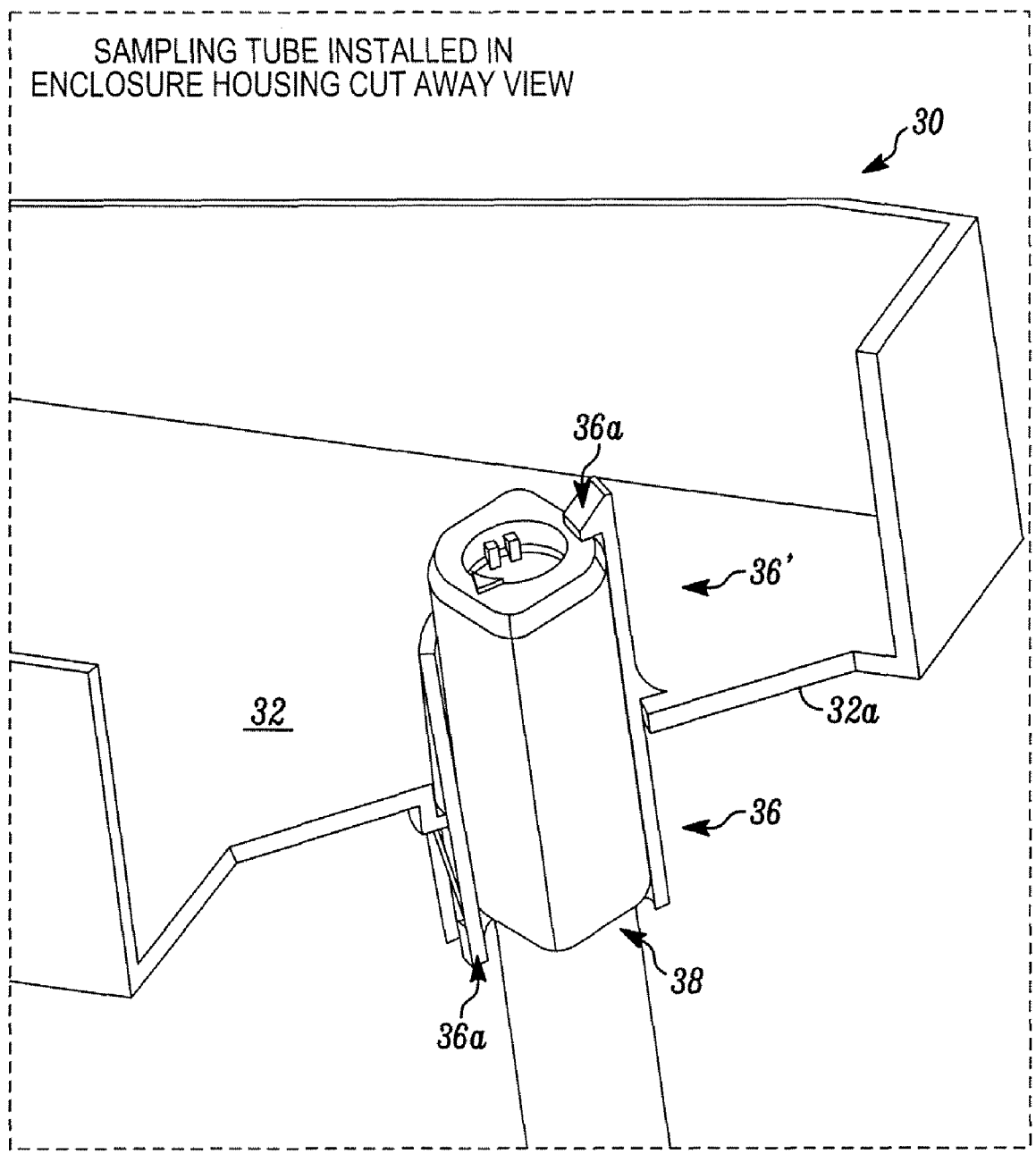
FIG. 10C illustrates some of the details of the sampling tube attachment structure.

FIGS. 10A-10C illustrate aspects of engagement of an assembled sampling tube, such as the embodiment illustrated in FIGS. 6A, 6B discussed above coupled to a housing or enclosure 32 of the duct-type detector 30. Those of skill in the art will understand the enclosure 32 contains an interior region which carries an ambient condition detector, such as a smoke or gas sensor 34.

The housing 32 also carries at least one and preferable two ports such as the port 36, 36' to which the sampling tube 38 is attached. Sampling tube 38 could correspond to any of the previously discussed embodiments without limitation. For discussion, the sampling tube 38 corresponds to the preferred embodiment of coupler 10-3 and conduit 12-3 of 6A, 6B without limitation.

In FIG. 10A, the respective sampling tube 38 is illustrated being slideably attached to an exterior part 36 of the port 36, 36' which is extending from a rear external surface 32a of the enclosure or housing 32. With the configuration of FIG. 10A the sampling tube 38 can be slid into position in the port 36, 36' to slideably engage a snap lock element 36a without having to remove a front cover or panel of the housing 32.

The port 36, 36' is formed with a predetermined internal cross-section 36b which permits the coupler 10-3 to be inserted thereinto only with selected orientations. The combination of the exterior cross-sectional shape of the coupler 10-3, and the internal cross-section 36b of the port 36 insures that the openings in the conduit 12-3 (intended to receive either inflowing or outflowing ambient atmosphere) are properly aligned relative to the orientation of the housing 32. A visual indicator can be carried on the coupler 10-3, for example, to provide visual confirmation that the axially oriented openings in the conduit 12-3 are properly aligned with the expected direction of flow of ambient atmosphere in the respective duct.

One or more latches corresponding to the latch 36a can be provided in the port 36, 36'. The latch or latches 36a lock the coupler 10-3 to the housing 32 and prevent disengagement or inadvertent removal thereof. The latch or latches 36a are readily actuatable by hand, without any need for tools. The respective coupler/conduit combination, such as the sampling tube 38, can be readily removed for cleaning or repositioning depending on the requirements.

FIG. 10B illustrates installation of the respective sampling tube 38 where the cover has been removed from the housing 32. In this instance, the conduit 12-3 is slid through the interior portion 36' of the port 36,36' and the coupler 10-3 subsequently slideably engages the respective latch or latches such as the latch 36a. It will be understood that the interior form 36 of FIG. 10A could be identical to the interior 36' of 10B without departing from the spirit and scope of the present invention. Alternately, the portions of the port 36, 36' could be configured differently from one another. In the installation illustrated in FIG. 10B, once the sampling tube 38 has been inserted through the interior 36' and locked into place, as described previously, the detector 30 would be closed by a front panel or cover not illustrated.

Figure 11A:
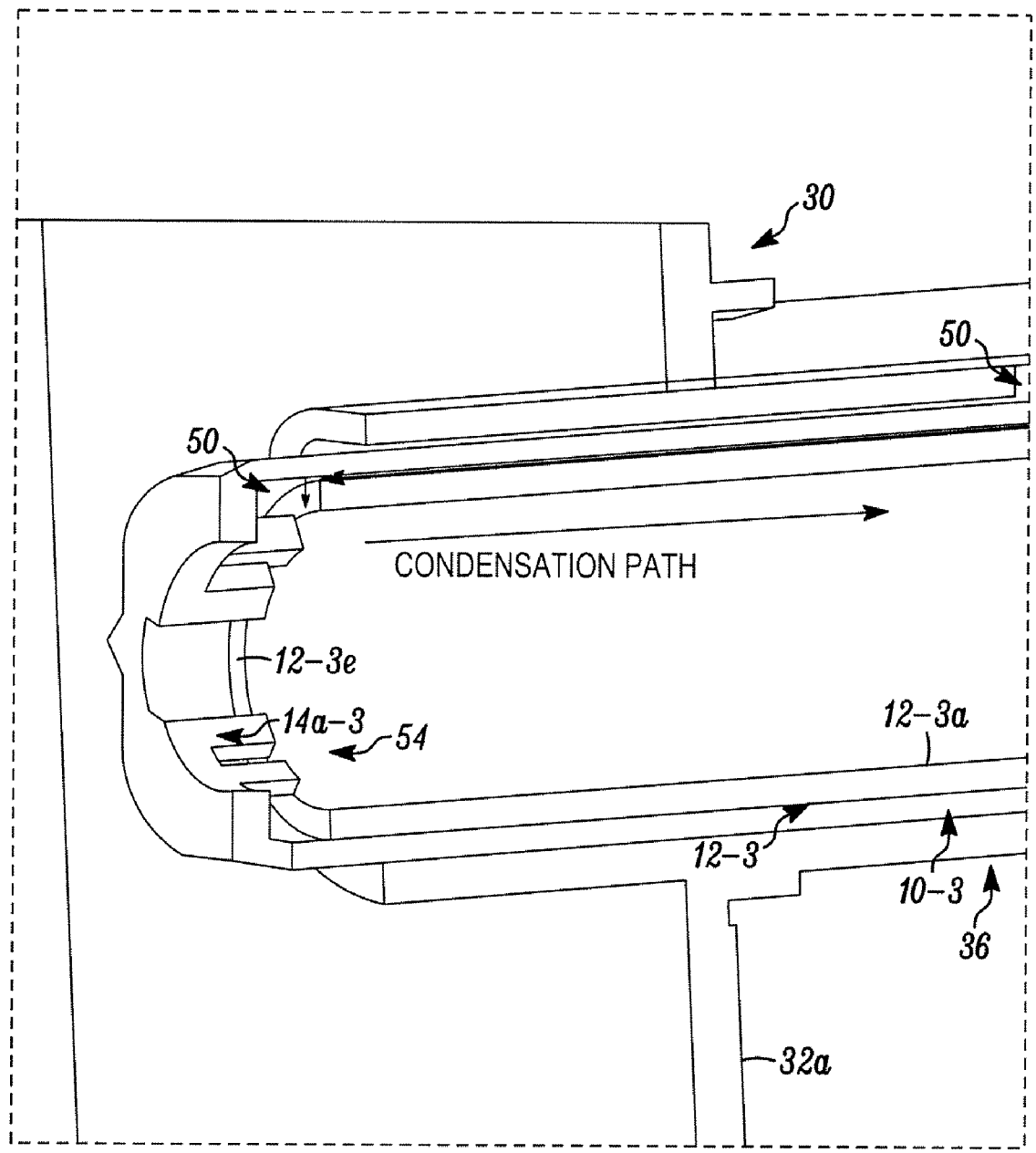
FIGS. 11A, 11B taken together illustrate condensation elimination paths formed in sampling tubes in accordance with the invention.
Figure 11B:
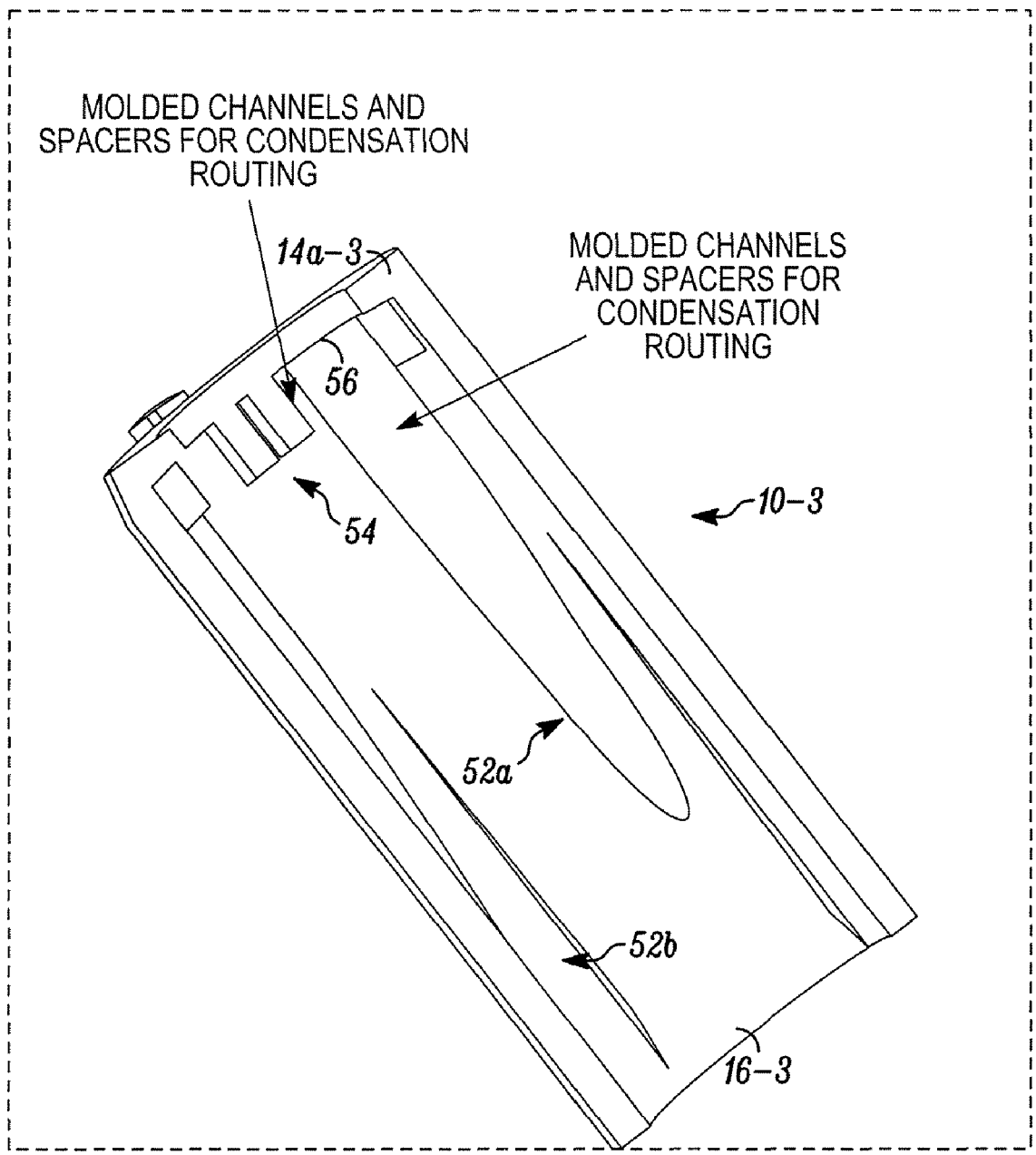

As illustrated in FIG. 11A, hollow conduit 12-3 which has been slideably received in coupler 10-3 together define an annular space 50 which extends along an external periphery of the conduit 12-3 and along an interior periphery of the coupler 10-3. This clearance between those surfaces provides a pathway for condensation, which may collect on the conduit 12-3, to flow away from the housing 30. This process can be enhanced by, as illustrated in FIG. 11B, by molding channels 52a, 52b into the internal peripheral surface 16-3 of the coupler 10-3.

One or more spacers 54 can also be molded into the end 14a-3 of the coupler 10-3 to offset an end surface 12-3e of the conduit 12-3 from an annular end surface 56 of the coupler 10-3. This space provides an additional part of the condensation exit path.

The condensation can then exit along the internal channel 12-3a of the conduit 12-3. The subject condensation tends to collect on the exterior surface of the tube or conduit 12-3 and then is forced toward the housing 30 of the detector due to airflow in the duct.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

The invention claimed is:

1. A detector comprising:
    a housing with at least one ingress port for ambient atmosphere extending through a wall of the housing and a hollow sampling tube detachably coupled to the housing;
    said at least one ingress port having a first latch;
    the hollow sampling tube comprising a hollow coupling element and a hollow, elongated ambient atmosphere receiving conduit;
    said coupling element has a second latch;
    a first end of the coupling element is slidably received in said at least one ingress port and into said housing along an axis of insertion into the port, with at least one predetermined fixed orientation; and the conduit is removably attached to a second end of the coupling element without extending through the coupling element, said coupling extends only from said second end of the coupling element;

wherein opposing surfaces of the coupling element and port lying parallel to the axis of insertion each have at least one flattened area that engage during coupling to align the coupling element and port into the at least one predetermined fixed orientation and wherein during use the coupling element is removable from the ingress port by hand without tools for cleaning.

2. A detector as in claim 1 where the housing is hollow and carries therein at least one of a smoke or gas sensor.

3. A detector as in claim 1 where the sampling tube lockingly engages the port with the fixed orientation.

4. A detector as in claim 1 where the sampling tube is slidably received in the port with one of a plurality of predetermined, fixed orientations.

5. A detector as in claim 4 where the housing is hollow and carries therein at least one of a smoke or gas sensor.

6. A detector as in claim 1 where the coupling element and the conduit engage one another with a predetermined, fixed orientation.

7. A detector as in claim 6 where the coupling element and the conduit engage with at least one of a rotary coupling, a snap-fix, or an interference fit.

8. A detector as in claim 6 where the coupling element releasably engages the port with the predetermined, fixed orientation.

9. A detector as in claim 8 where the housing is hollow and carries therein at least one of a smoke or gas sensor.

10. A detector as in claim 9 where the coupling element engages the port without the conduit first being art ached thereto.

11. A detector as in claim 9 where the coupling element engages the port subsequent to the conduit being attached thereto.

12. A detector as in claim 8 where the housing includes a second, egress port, and a second sampling tube coupled thereto with a conduit.

13. A detector as in claim 12 which includes at least one flow path between the coupling element and the conduit to direct condensation from the housing.

14. A detector as in claim 1 which includes at least one flow path between the coupling element and the conduit to direct condensation from the housing.

15. A multi-element sampling tube comprising
an elongated, hollow, cylindrical connector with first and second ends,
the connector has a latch to removably attach and is configured to mate, with a predetermined orientation with a duct-type detector;
an aperture on an outside surface of the connector that receives a latch for holding the connector within a port of the detector; and a hollow conduit that extends only from the second end of the connector and slidably engages the connector with a fixed orientation without extending through the coupling element wherein during use the connector is removable from the port of the detector by hand without tools for cleaning.

16. A sampling tube as in claim 15 where the connector has a non-circular cross-section that mates with, and attaches to the duct-type detector.

17. A sampling tube as in claim 15 where the connector includes at least one channel to carry condensation.

18. A sampling tube as in claim 15 where the connector includes axially extending spacers which limit travel of the tube conduit into the connector.

19. An apparatus as in claim 15 further comprising at least one channel disposed on the conduit to carry condensation.

20. An apparatus comprising:
a duct detector housing with at least one ingress port for ambient atmosphere;
a hollow sampling tube comprising; a coupler and a hollow conduit;
said coupler disposed on an end of the sampling tube, the coupler is slidably received in the port along an axis of insertion, with at least one predetermined, fixed orientation wherein mating surfaces of the coupler and port lying parallel to the axis of insertion each have at least one flattened area that engage during insertion to align the coupler and port into at least one predetermined fixed orientation;
said hollow conduit extends only from the second end of the coupler and slidably engages the coupler with a fixed orientation without extending through the coupling element; and
at least one channel disposed on the tube between the coupler and conduit to carry condensation wherein the coupler and tube is are inserted into and slidably locked into the duct detector housing from the exterior surface thereof and wherein during use the coupler and conduit are removable from the port by hand without tools for cleaning.

21. An apparatus as in claim 20 further comprising:
a coupling element having a coupling housing;
a first end of the coupling housing having a connecting member, the connecting member selected from a class of an integrally formed flexible attachment element, a cantilever snap, an integrally molded thread, a molded opening, a molded formed feature, or a depression; and
a second end of the coupling housing having a locking aperture wherein the first end of the coupling housing engages the sampling tube and the second end of the coupling housing engages the duct detector housing.

* * * * *